US012642646B2

(12) United States Patent
Hallen

(10) Patent No.: US 12,642,646 B2
(45) Date of Patent: Jun. 2, 2026

(54) SYSTEMS AND METHODS FOR VITREOUS DISEASE SEVERITY MEASUREMENT

(71) Applicant: Alcon Inc., Fribourg (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 742 days.

(21) Appl. No.: 18/054,424

(22) Filed: Nov. 10, 2022

(65) Prior Publication Data

US 2023/0157811 A1 May 25, 2023

Related U.S. Application Data

(60) Provisional application No. 63/281,286, filed on Nov. 19, 2021.

(51) Int. Cl.
| | |
|---|---|
| *A61F 2/16* | (2006.01) |
| *A61B 3/10* | (2006.01) |
| *A61B 3/107* | (2006.01) |

(52) U.S. Cl.
CPC .............. *A61F 2/16* (2013.01); *A61B 3/1005* (2013.01); *A61B 3/102* (2013.01); *A61B 3/107* (2013.01)

(58) Field of Classification Search
CPC ......... A61F 2/16; A61B 3/1005; A61B 3/102; A61B 3/0025
See application file for complete search history.

(56) References Cited

U.S. PATENT DOCUMENTS

| | | |
|---|---|---|
| 3,780,979 A | 12/1973 | De Guillebon |
| 4,357,088 A | 11/1982 | Pomerantzeff |

| | | |
|---|---|---|
| 5,312,396 A | 5/1994 | Feld |
| 5,909,270 A | 6/1999 | Moser |
| 6,142,630 A | 11/2000 | Koester |
| 6,322,556 B1 | 11/2001 | Gwon |
| 6,789,900 B2 | 9/2004 | Van De Velde |
| 7,374,287 B2 | 5/2008 | Van De Velde |
| 7,510,282 B2 | 3/2009 | Ueno |
| 7,520,613 B2 | 4/2009 | Saito et al. |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Blake F. Webb, et al.; "Prevalence of vitreous floaters in a community sample of smartphone users"; Internat'l Journal of Ophthalmology; Jun. 18, 2013; pp. 402-405; 6(3); PMC/ US National Library of Medicine National Institutes of Health.

(Continued)

*Primary Examiner* — John R Wallace
(74) *Attorney, Agent, or Firm* — Patterson + Sheridan, LLP

(57) ABSTRACT

Certain aspects presented herein provide systems and methods utilizing one or more machine learning models in determining a severity of vitreous disease, and in particular, vitreous opacities. Such machine learning models are trained based on historical patient data to determine the severity of vitreous opacities afflicting a current patient. The severity determination may thereafter be utilized to inform treatment decisions for the current patient, including patient suitability for certain types of treatment.

30 Claims, 6 Drawing Sheets

(56)                    References Cited

U.S. PATENT DOCUMENTS

| | | | |
|---|---|---|---|
| 7,703,922 | B2 | 4/2010 | Van De Velde |
| 8,480,659 | B2 | 7/2013 | Frey et al. |
| 8,652,602 | B1 | 2/2014 | Dolla |
| 8,783,868 | B2 | 7/2014 | Qiu |
| 8,876,808 | B2 | 11/2014 | Feklistov et al. |
| 8,994,753 | B2 | 3/2015 | Nakano |
| 9,033,500 | B2 | 5/2015 | Utsunomiya |
| 9,603,519 | B2 | 3/2017 | Bor et al. |
| 9,675,243 | B2 | 6/2017 | Sasak et al. |
| 9,789,002 | B2 | 10/2017 | Van De Velde |
| 10,130,511 | B2 | 11/2018 | Dantus |
| 10,478,342 | B2 | 11/2019 | Dick |
| 10,555,835 | B2 | 2/2020 | Schuele et al. |
| 2007/0258094 | A1 | 11/2007 | Izatt et al. |
| 2007/0291277 | A1 | 12/2007 | Everett |
| 2009/0073384 | A1 | 3/2009 | Warden |
| 2009/0137989 | A1 | 5/2009 | Kataoka |
| 2009/0196477 | A1 | 8/2009 | Cense et al. |
| 2010/0123873 | A1 | 5/2010 | Raymond |
| 2010/0152847 | A1 | 6/2010 | Padrick |
| 2011/0077557 | A1 | 3/2011 | Wing et al. |
| 2012/0281235 | A1 | 11/2012 | Murata |
| 2013/0131652 | A1 | 5/2013 | Dick |
| 2013/0173029 | A1 | 7/2013 | Caldeira et al. |
| 2014/0058367 | A1 | 2/2014 | Dantus |
| 2014/0216468 | A1 | 8/2014 | Goldshleger |
| 2014/0257257 | A1 | 9/2014 | Grant et al. |
| 2014/0268036 | A1* | 9/2014 | Ketterling ............. G16H 50/30 |
| | | | 351/205 |
| 2014/0276674 | A1 | 9/2014 | Lee |
| 2015/0190278 | A1 | 7/2015 | Gooding |
| 2015/0342782 | A1 | 12/2015 | Mordaunt |
| 2016/0058617 | A1 | 3/2016 | Luttrull et al. |
| 2016/0074214 | A1 | 3/2016 | Palanker et al. |
| 2016/0074221 | A1 | 3/2016 | Tassignon et al. |
| 2016/0166431 | A1 | 6/2016 | Vogler et al. |
| 2016/0227999 | A1 | 8/2016 | An et al. |
| 2016/0235588 | A1 | 8/2016 | Hart et al. |
| 2016/0256324 | A1 | 9/2016 | Suzuki |
| 2016/0278629 | A1 | 9/2016 | Schuele |
| 2016/0302969 | A1 | 10/2016 | Yamamoto |
| 2017/0181625 | A1 | 6/2017 | Kawakami et al. |
| 2017/0252213 | A1 | 9/2017 | Furuuchi et al. |
| 2017/0326003 | A1 | 11/2017 | Schuele et al. |
| 2018/0014777 | A1* | 1/2018 | Amir ................... A61M 35/003 |
| 2018/0028354 | A1 | 2/2018 | Heeren |
| 2018/0028355 | A1 | 2/2018 | Raksi |
| 2018/0140257 | A1 | 5/2018 | Govindjee et al. |
| 2018/0206719 | A1 | 7/2018 | Adler et al. |
| 2018/0317767 | A1 | 11/2018 | Ryan |
| 2018/0353064 | A1 | 12/2018 | Soetikno et al. |
| 2018/0368915 | A1 | 12/2018 | Xia et al. |
| 2019/0159933 | A1 | 5/2019 | Romano et al. |
| 2019/0282403 | A1 | 9/2019 | Barrett et al. |
| 2019/0290124 | A1 | 9/2019 | Laforest et al. |
| 2019/0313903 | A1 | 10/2019 | Mckinnon |
| 2019/0365569 | A1 | 12/2019 | Skovgaard et al. |
| 2020/0038241 | A1 | 2/2020 | Wang et al. |
| 2020/0060873 | A1 | 2/2020 | Heeren |
| 2020/0085292 | A1 | 3/2020 | Fukuma et al. |
| 2020/0129336 | A1 | 4/2020 | Schuele et al. |
| 2020/0130103 | A1 | 4/2020 | Choi |
| 2020/0192080 | A1 | 6/2020 | Karam |
| 2020/0196853 | A1 | 6/2020 | Van Hemert et al. |
| 2020/0273218 | A1 | 8/2020 | Camino et al. |
| 2020/0397289 | A1 | 12/2020 | Ralston |
| 2020/0400422 | A1 | 12/2020 | Ralston |
| 2021/0100450 | A1 | 4/2021 | Amma |
| 2021/0186753 | A1 | 6/2021 | Al-Qaisi et al. |
| 2021/0275009 | A1 | 9/2021 | Yates |
| 2021/0338595 | A1* | 11/2021 | De Smedt .......... A61F 9/00802 |
| 2021/0378507 | A1 | 12/2021 | Wallace |
| 2021/0386586 | A1 | 12/2021 | Bor |

| | | | |
|---|---|---|---|
| 2022/0012459 | A1 | 1/2022 | Schwiegerling |
| 2022/0031511 | A1 | 2/2022 | Charles |
| 2023/0157889 | A1 | 5/2023 | Bor |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |

(56)         References Cited

FOREIGN PATENT DOCUMENTS

| WO | 2023089459 A1 | 5/2023 |
| WO | 2023097391 A1 | 6/2023 |

OTHER PUBLICATIONS

Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.

Ellex Website, Treatment Guidelines—Laser Floater Removal; 2016, Ellex Medical Pty Ltd. E&OE. VB0002E, downloaded Apr. 20, 2017.

Felix Sauvage et al: "Photoablation of Human Vitreous Opacities by Light—Induced Vapor Nanobubbles", ACS Nano, vol. 13, No. 7, Jul. 9, 2019, pp. 8401-8416.

Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.

Michael J. Escuti, et al., "Geometric-Phase Holograms", Optics & Photonics News, pp. 22-29, Feb. 2016.

Milston Rebecca et al: "Vitreous floaters: Etiology, diagnostics, and management", Survey of Ophthalmology, vol. 61, No. 2, Mar. 1, 2016, pp. 211-227.

Nicusor Iftimia et al: "Hybrid retinal imaginer using line-scanning laser ophthalmoscopy and spectral domain optical coherence tomography", Optics Express, vol. 14, No. 26, Dec. 22, 2006.

Reece Bergstrom, et al., Vitreous Floaters, National Center for Biotechnology Information, May 21, 2020, 4 pages, Bookshelf ID NBK470420, StatPearls Publishing LLC, online.

Wikipedia Encyclopedia, Floater, Wikipedia Encyclopedia, Mar. 29, 2021, online: https://en.wikipedia.org/wiki/floater?wprov=sfti 1.

Zhang Yunbo et al: "Parallel large-range scanning confocal microscope based on a digital micromirror device", Optik vol. 124, No. 13 (2013), Aug. 4, 2012, pp. 1585-1588.

Damodaran et al., "Digital micromirror device based ophthalmoscope with concentric circle scanning", 2017, pp. 2766-2780, vol. 8, No. 5, Biomedical Optics Express.

Fischer et al., "Scanning Laser Ophthalmoscopy (SLO)", In: Bille JF, editor. High Resolution Imaging in Microscopy and Ophthalmology: New Frontiers in Biomedical Optics [Internet], Aug. 14, 2019, accessed on Jan. 30, 2023 from https://www.ncbi.nlm.nih.gov/books/NBK554043, Springer.

Ginner et al., "Wide-Field OCT Angiography at 400 KHz Utilizing Spectral Splitting", Photonics, Oct. 23, 2014, pp. 369-379, vol. 1, No. 4.

Heidelberg Engineering GMBH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/us/en/products/spectralis/spectralis/.

Hofer et al., "Dispersion encoded full range frequency domain optical coherence tomography", Jan. 5, 2009, pp. 7-24, vol. 17, No. 1, Optics Express, US.

Hofer et al., "Fast dispersion encoded full range optical coherence tomography for retinal imaging at 800 nm and 1060 nm", Mar. 1, 2010, pp. 4898-4919, vol. 18, No. 5, Optics Express.

Leitgeb et al., "Complex ambiguity-free Fourier domain optical coherence tomography through transverse scanning", 2007, pp. 3453-3455, vol. 32, Optics Letters.

Li et al., "DMD-based three-dimensional chromatic confocal microscopy", 2020, pp. 4349-4356, vol. 59, No. 14, Applied Optics.

Martial et al., "Programmable Illumination and High-Speed, Multi-Wavelength, Confocal Microscopy Using a Digital Micromirror", Aug. 2012, e43942, vol. 7, No. 8, PLOS One.

Reznicek Lukas et al., "Wide-Field Megahertz OCT Imaging of Patients with Diabetic Retinopathy", Journal of Diabetes Research, 2015, 5 pages.

Ruggeri et al., "Imaging and full-length biometry of the eye during accommodation using spectral domain OCT with an optical switch", Jul. 1, 2012, pp. 1506-1520, vol. 3, No. 7, Biomedical Optics Express.

Sarunic et al., "Instantaneous complex conjugate resolved spectral domain and swept-source OCT using 3x3 fiber couplers", Feb. 2005, pp. 957-967, vol. 13, No. 3, Optics Express.

Shields et al., "Wide-angle Imaging of the Ocular Fundus", Review of the Ophthalmology, Feb. 15, 2003.

Singh, "Lasers Take Aim at Floaters", Ophthalmology Management, Jul. 1, 2019, pp. 38, 40-42, 59, vol. 23.

Singh, "Modern vitreolysis—YAG laser treatment now a real solution for the treatment of symptomatic floaters", Survey of Ophthalmology, Mar. 3, 2020, pp. 581-591, vol. 65, No. 5.

SunLED, NanoPoint-0201 Series LEDs, published Feb. 15, 2016, www.SunLEDusa.com.

Volk Optical, "Volk Idrees Mid-Vitreous Lens", Dec. 20, 2020, accessed on Dec. 20, 2020 from https://www.volk.com/ . . . s?pr_prod_strat=collection_fallbackpr_rec_pid=4513049018402&or_ref_pid=4513048952866pr_seq=uniform.

Volk Optical, "Volk Singh Mid-Vitreous Lens", Dec. 20, 2020, accessed on Dec. 20, 2020 from https://www.volk.com/products/singh-mid-vitreous-vitreous-slit-lamp-lens?_pos=3&amp;_sid=b50c0674famp;amp;_ss=I.

Wang et al., "In vivo full range complex Fourier domain optical coherence tomography", Jan. 30, 2007, 054103, vol. 90, Applied Physics Letters.

Wojtkowski et al., "Full range complex spectral optical coherence tomography technique in eye imaging", 2002, pp. 1415-1417, vol. 27, No. 16, Optics Letters.

Yasuno et al., "Simultaneous B—M-mode scanning method for real-time full-range Fourier domain optical coherence tomography", 2006, pp. 1861-1865, vol. 45, No. 8, Applied Optics.

Zhang et al., Removal of a mirror image and enhancement of the signal-to-noise ratio in Fourier-domain optical coherence tomography using an electro-optic phase modulator, Jan. 15, 2005, vol. 30, No. 2, Optics Letters.

Zhou et al., "Dual channel dual focus optical coherence tomography for imaging accommodation of the eye", May 25, 2009, pp. 8947-8955, vol. 17, No. 11, Optics Express.

Adrian G.H. Podoleanu et al., Combined optical coherence tomograph and scanning laser ophthalmoscope mi nije dostupan besplatno., Electronics Letters, 34 (11), 1998.

Chi-Hung Lee, et al., Imaging vitreous floaters and cataracts with optical simulations, Optik, 194, 1-9, 2019.

Christy K. Sheehy et al., High-speed, image-based eye tracking with a scanning laser ophthalmoscope, Biomedical Optics Express, vol. 3, No. 10, 2012.

D. H. Kelly, "Retinal Inhomogeneity. II. Spatial Summation," J. Opt. Soc. Am., pp. 114-119, vol. 1, No. 1 (Jan. 1984).

D. H. Kelly, "Retinal Inhomogeneity. III. Circular-Retina Theory," D.H. Kelly, J. Opt. Soc. Am., pp. 810-819, vol. 2, No. 6 (Jun. 1985).

D.H. Kelly, "Visual Processing of Moving Stimuli," J. Opt. Soc. Am., pp. 216-225, vol. 2, No. 2 (Feb. 1985).

D.H. Kelly,, "Motion and Vision. II. Stabilized Spatio-Temporal Threshold Surface," J. Opt. Soc. Am., pp. 1340-1349, vol. 69, No. 10 (Oct. 1979).

D.H.Kelly, "Retinal Inhomogeneity. I. Spatiotemporal Contrast Sensitivity," J. Opt. Sec. Am., pp. 107-113, vol. 1, No. 1 (Jan. 1984).

Mojana F. et al.. Observations by spectral-domain optical coherence tomography combined with simultaneous scanning laser ophthalmoscopy: imaging of the vitreous, American Journal of Ophthalmol. Apr. 2010; 149(4):641-650.

Nidek, Scanning Laser Ophthalmoscope Mirante SLO/OCT Mirante SLO, https://www.nidek-intl.com/product/ophthaloptom/diagnostic/dia_retina/mirante.htm.

Peter G. J. Barten, "Contrast Sensitivity of the Human Eye and its Effects on Image Quality," Chapter 3, pp. 27-40, Model for the spatial contrast sensitivity of the eye, (1999).

Pointer, J. S., & Hess, R. F. "The contrast sensitivity gradient across the human visual field: With emphasis on the low spatial frequency range.", R. F. Vision Research, 29(9), 1133-1151 (1989).

Sebag J et al., Vitreous and Vitreoretinal Interface, Ch. 21, 2015.

(56) References Cited

OTHER PUBLICATIONS

Sebag J., Vitreous and Vision Degrading Myodesopsia. Progress in Retinal and Eye Research Nov. 2020;79.

T Ivanova et al., Vitrectomy for primary symptomatic vitreous opacities: an evidence-based review, Eye (Lond) May 2016;30(5):645-55.

Teri T Kleinberg et al., Vitreous substitutes: a comprehensive review, Survey of Ophthalmology, 56 (4), 2011.

\* cited by examiner

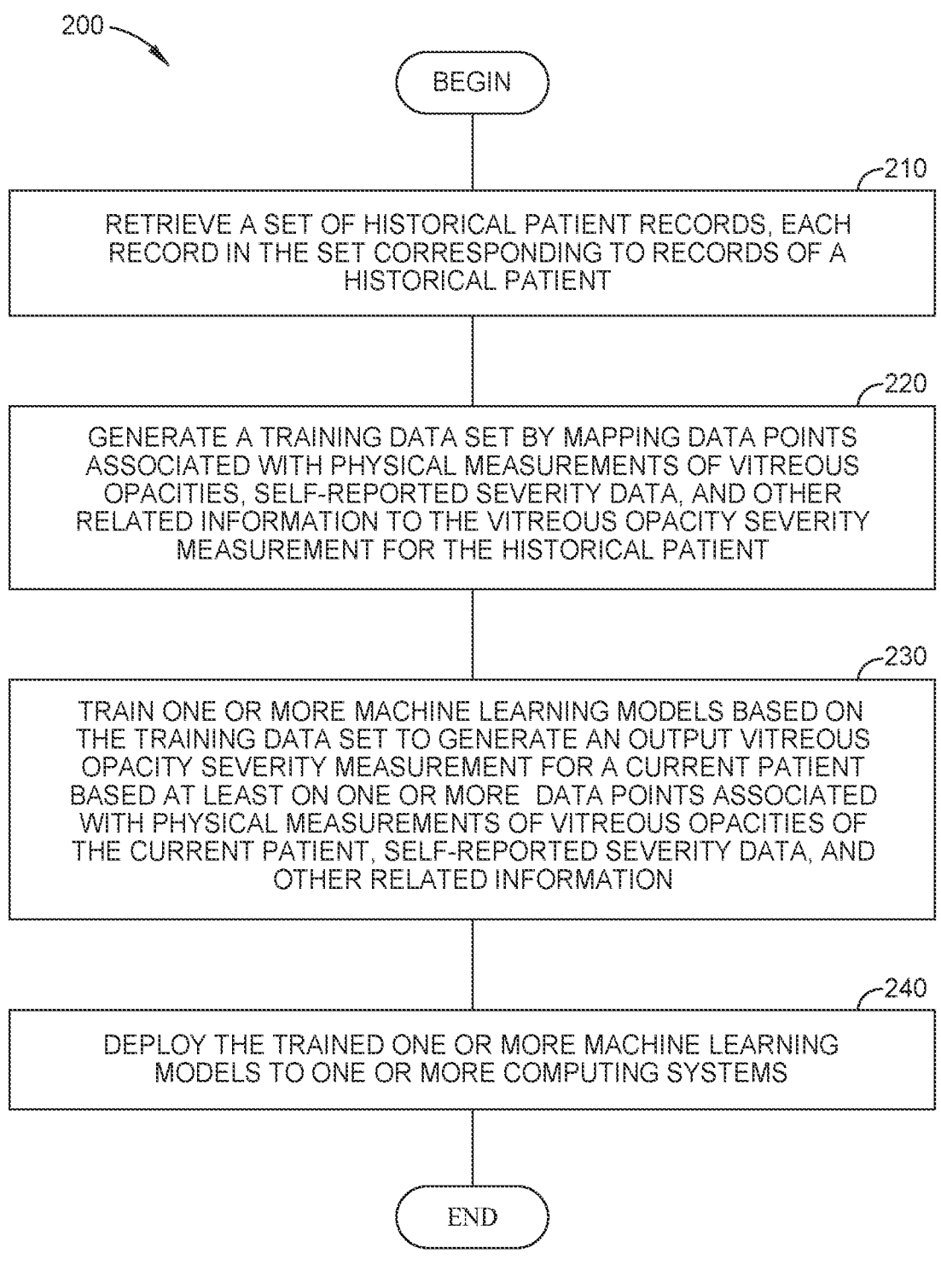

200

BEGIN

210

RETRIEVE A SET OF HISTORICAL PATIENT RECORDS, EACH RECORD IN THE SET CORRESPONDING TO RECORDS OF A HISTORICAL PATIENT

220

GENERATE A TRAINING DATA SET BY MAPPING DATA POINTS ASSOCIATED WITH PHYSICAL MEASUREMENTS OF VITREOUS OPACITIES, SELF-REPORTED SEVERITY DATA, AND OTHER RELATED INFORMATION TO THE VITREOUS OPACITY SEVERITY MEASUREMENT FOR THE HISTORICAL PATIENT

230

TRAIN ONE OR MORE MACHINE LEARNING MODELS BASED ON THE TRAINING DATA SET TO GENERATE AN OUTPUT VITREOUS OPACITY SEVERITY MEASUREMENT FOR A CURRENT PATIENT BASED AT LEAST ON ONE OR MORE DATA POINTS ASSOCIATED WITH PHYSICAL MEASUREMENTS OF VITREOUS OPACITIES OF THE CURRENT PATIENT, SELF-REPORTED SEVERITY DATA, AND OTHER RELATED INFORMATION

240

DEPLOY THE TRAINED ONE OR MORE MACHINE LEARNING MODELS TO ONE OR MORE COMPUTING SYSTEMS

END

FIG. 2

SYSTEMS AND METHODS FOR VITREOUS DISEASE SEVERITY MEASUREMENT

BACKGROUND

The vitreous body is a hydrophilic gel located between the crystalline lens and the retina, constituting the largest volumetric component of the human eye. Healthy vitreous is optically transparent, composed mostly of water, with a low concentration of macromolecules (collagen, soluble proteins, and hyaluronan) that provide structural support to the globe and stability during rapid eye movements and strenuous physical activity. The optical transparency of the vitreous body is the result of the organization of these molecular components. In addition to providing structural support for the eye and facilitating light transmission, vitreous is important in ocular physiology as a repository for anti-oxidants and a pathway for nutrients utilized by the crystalline lens, ciliary body, and the retina.

With age, the vitreous undergoes fibrous degeneration and gel liquefaction, which in certain cases may lead to detachment of the vitreous from the retina in a process known as posterior vitreous detachment (PVD). Fibrous vitreous liquefaction results from molecular changes causing dissociation of collagen from hyaluronan, forming liquid vitreous and causing cross-linking of collagen fibrils into visible fibers. Other conditions that may quicken the onset of such molecular changes include myopia (nearsightedness), eye trauma, and previous cataract surgeries.

The formation of liquefied pockets, aggregation of collagen fibrils into larger fibers, and detachment of vitreous from the retina results in opacities in the vitreous, also known as "floaters." Vitreous opacities may scatter light entering the eye, thus appearing as spots, shadows, cobwebs, or other assorted shapes that appear to move about in the field of vision of the patient. Vitreous opacities are one of the most common, albeit least treated, ocular conditions. Although symptoms are minimal in most patients and do not require treatment, vitreous opacities can, in certain cases, cause significant disturbances in vision, thereby impairing the vision-related quality of life (QOL) for some patients. When the severity of visual disturbance is significant, vitreous opacities may be treated with, e.g., laser vitreolysis and small-gauge vitrectomy.

Currently, various optical techniques are utilized to clinically characterize and grade vitreous opacities, in addition to patient self-reporting. Such optical techniques include utilization of a hand-held lens in combination with, e.g., slit illumination, to optically view the vitreous opacities. However, these techniques provide marginal and variable results, and do not provide an objective quantification of the degree of visual impairment caused by vitreous opacities, leading to inconsistent characterization and grading thereof. Also, patient self-reporting is subjective and, in some cases, fails to indicate the true degree of visual impairment. As a result, it is often difficult to determine whether a patient's occurrence of vitreous opacities appropriates treatment.

Accordingly, what is needed in the art are improved systems and methods for determining severity of vitreous disease to inform patient suitability for treatment.

SUMMARY

According to certain embodiments, a method of determining a severity of a vitreous opacity condition is provided. The method comprises generating, using one or more diagnostic devices, one or more data points associated with measurements of physical parameters of a vitreous opacity condition of a current patient; and generating, using one or more trained machine learning models, one or more diagnostic determinations including a severity score of the vitreous opacity condition based, at least in part, on the one or more data points associated with measurements of physical parameters of the vitreous opacity condition of the current patient, wherein: the one or more trained machine learning models are trained based on at least one historical dataset, wherein each entry in the historical data set includes one more data points associated with measurements of physical parameters of a vitreous opacity condition for a historical patient mapped to a diagnostic determination associated with the historical patient, wherein: the diagnostic determination associated with the historical patient includes a severity score of the vitreous opacity condition for the historical patient, and the physical parameters of the vitreous opacity condition for the historical patient comprise one or more of a number, a size, a shape, a surface area, a relative transparency, a movement, a location, and a distance to a retina and/or a crystalline lens of one or more vitreous opacities.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 2 illustrates example operations that may be performed by one or more computing systems to train one or more machine learning models to determine a severity of a patient's occurrence of vitreous opacities, in accordance with certain aspects described herein.

To facilitate understanding, identical reference numerals have been used, where possible, to designate identical elements that are common to the Figures. It is contemplated that elements and features of one embodiment may be beneficially incorporated in other embodiments without further recitation.

DETAILED DESCRIPTION

Figure 1A:
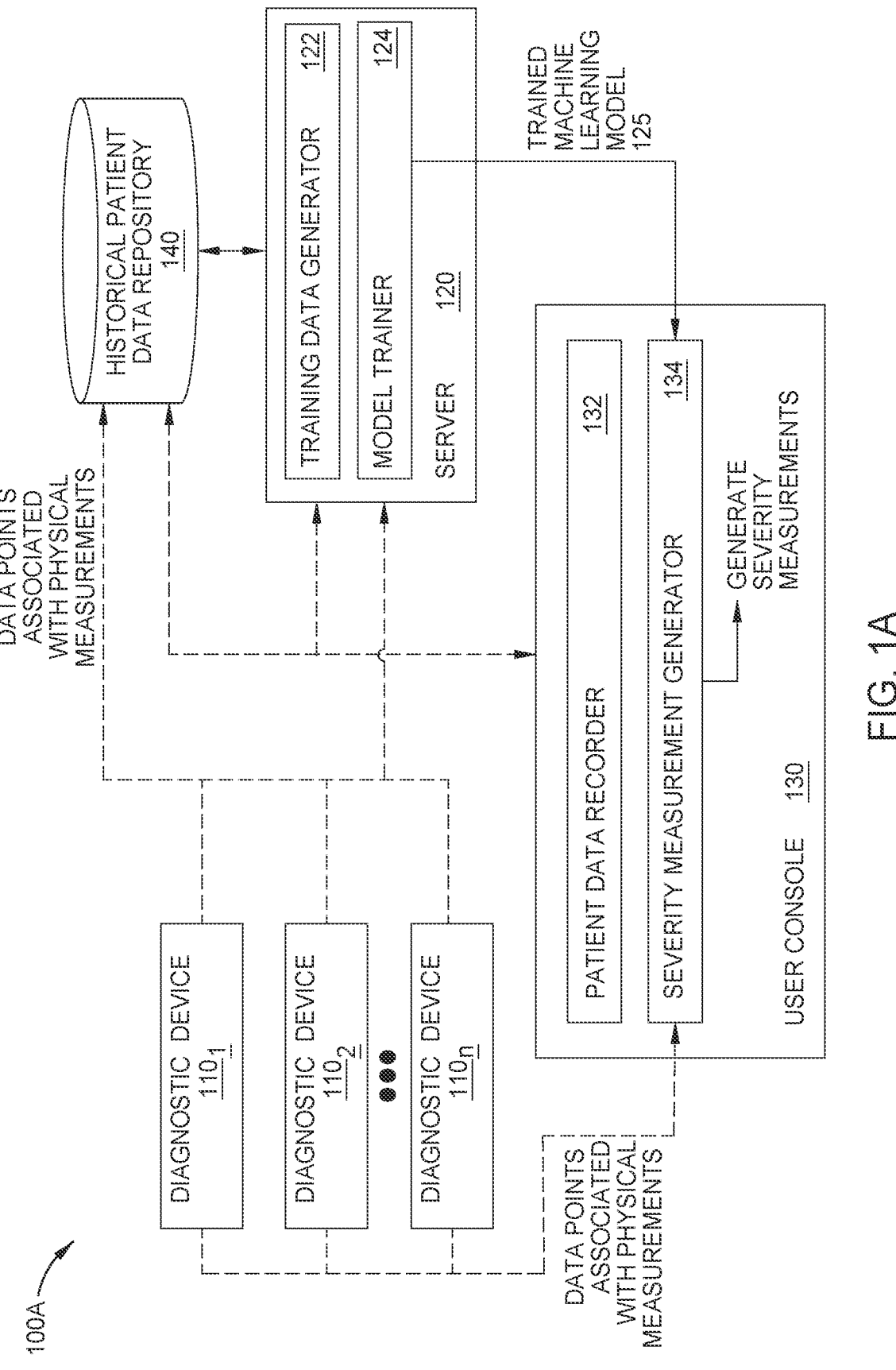
FIGS. 1A-1C depict an example environment in which one or more machine learning models are trained and deployed for use in determining a severity of a patient's vitreous opacity condition, in accordance with certain aspects described herein.

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

As used herein, the term "about" may refer to a +/−10% variation from the nominal value. It is to be understood that such a variation can be included in any value provided herein.

The present disclosure relates generally to systems and methods for determining a severity of vitreous disease, and more particularly, to systems and methods for determining a severity of vitreous opacities.

As discussed above, the presence of vitreous opacities is a common eye condition that is often challenging to effectively characterize the severity thereof. Vitreous opacities, also known as "floaters," are generally caused by fibrous degeneration and gel liquefaction, which may occur naturally with age. In a healthy eye, hyaluronan (i.e., hyaluronic acid) may prevent collagen fibrils from agglomerating in the vitreous cavity, thereby maintaining the structure and transparency of the vitreous. However, as the eye ages, hyaluronan may dissociate from collagen, causing cross-linking and aggregation of collagen fibrils, and forming pockets of liquid vitreous. These structures scatter light entering the eye, and may appear as assorted shapes and shadows in the field of vision of the patient.

Various optical techniques are currently utilized to help characterize and grade vitreous opacities, including microscopy, ultrasound imaging, and dynamic light scattering (DLS). However, such techniques only facilitate structural characterization of vitreous opacities, and do not provide a quantification of the degree of visual impairment caused thereby. There are currently no ophthalmic systems that are capable of objectively quantifying the degree of visual impairment caused by a patient's vitreous opacities, based on imaging data or other information associated with the patient. And, as previously discussed, patient self-reporting is subjective and in some cases fails to indicate the true degree of visual impairment. As a result, it is often difficult to determine whether a patient's vitreous opacity condition appropriates treatment.

Aspects presented herein provide systems and methods utilizing one or more machine learning models in determining a severity of vitreous opacities afflicting a patient to inform patient suitability for treatment. Such machine learning models are trained based on historical patient data associated with historical patients with various severities of the same or similar condition. By using these machine learning models, a large universe of historical patient data can be leveraged to determine a more accurate or objective indication of the severity of vitreous opacities afflicting a current patient. As defined herein, a current patient is generally a patient who is afflicted by the manifestation of vitreous opacities and for whom these machine learning models may be used to provide a severity measurement, e.g., a severity score, based on the current patient's information (e.g., imaging data). Using the severity measurement, a physician, e.g., ophthalmic surgeon, is able to determine whether the patient's condition is suitable for treatment, such as laser vitreolysis and small-gauge vitrectomy. Accordingly, the techniques herein improve existing ophthalmic systems, enabling them to objectively quantify the degree of visual impairment caused by a patient's vitreous opacity condition, based on imaging data and other information associated with the patient.

Example Computing Environment for Improving Vitreous Disease Diagnostics

Figure 1B:
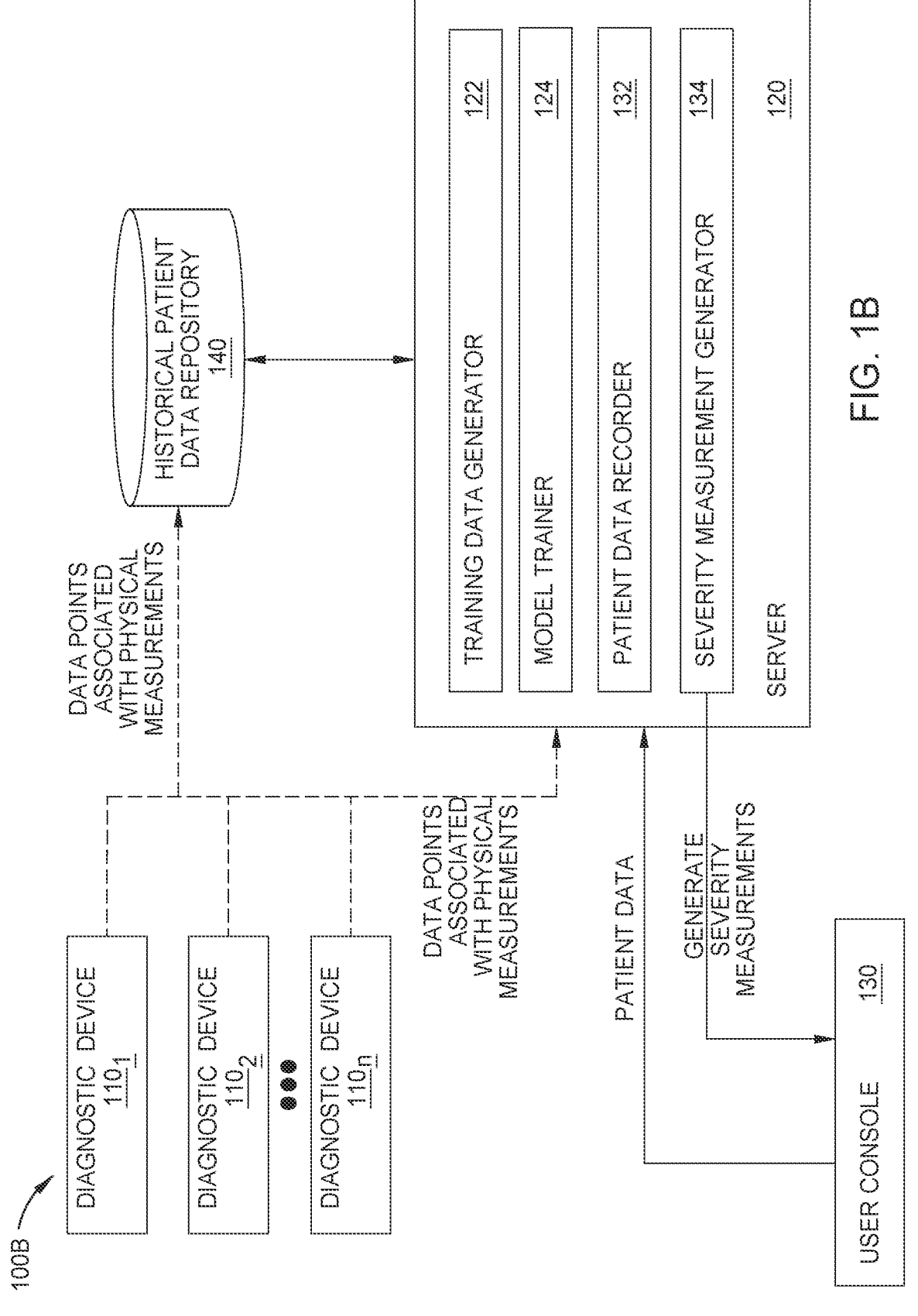
Figure 1C:
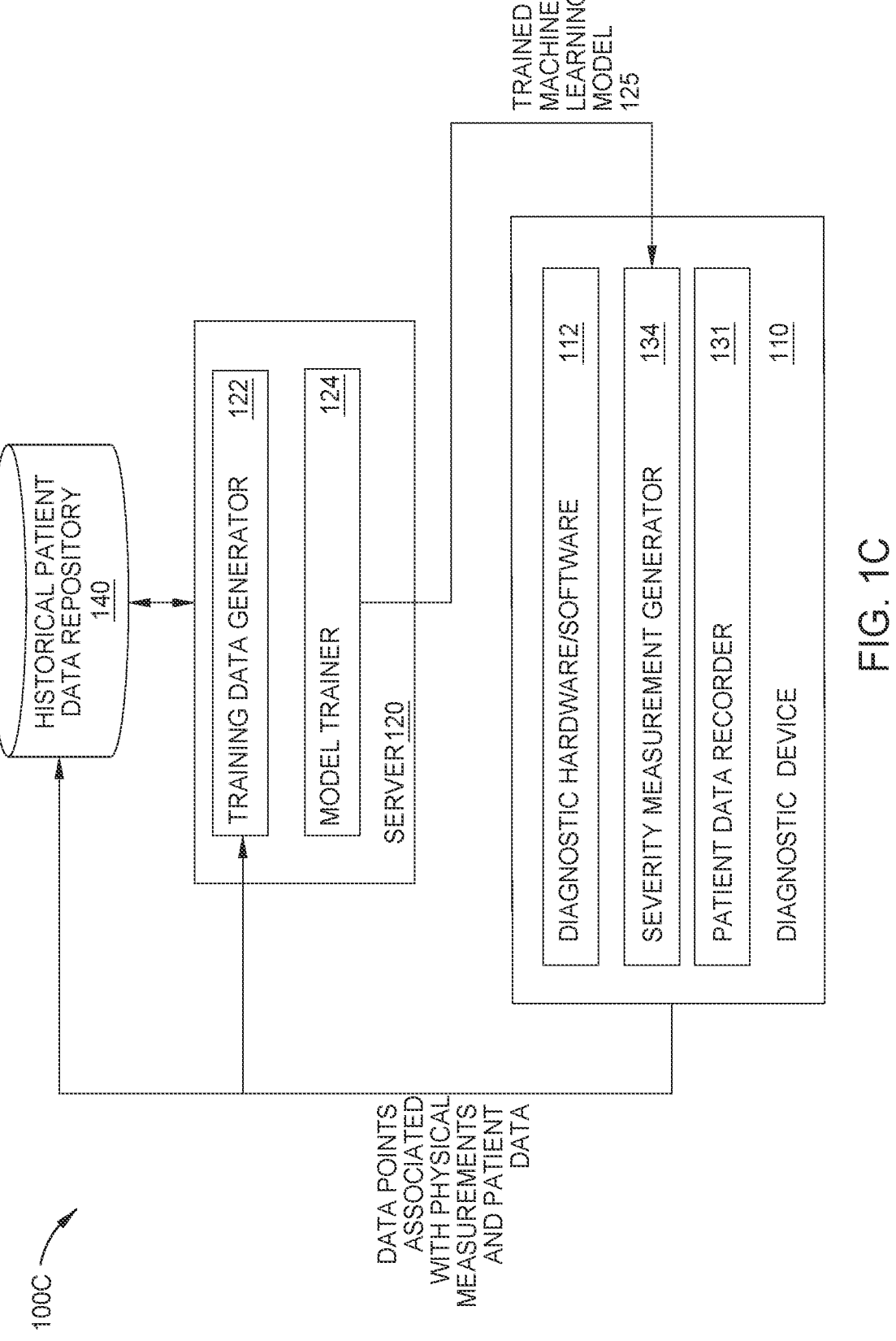

FIGS. 1A-1C illustrate example computing environments in which one or more machine learning models are trained and used in determining a severity of a patient's vitreous opacities or vitreous opacity condition (hereinafter "opacity condition"). Generally, these machine learning models may be trained using a corpus of training data including records corresponding to historical patient data and deployed for use in determining the severity of the patient's opacity condition. Historical patient data for each historical patient may include the patient's demographic information, recorded measurements of physical parameters of the patient's opacity condition pre-treatment, pre-treatment self-reported severity data, the patient's vitreous opacity severity measurements, information about the treatment, if any, such as the type of treatment, and/or post-treatment self-reported severity data, as well as other post-treatment information, such as measurements of physical parameters of the patient's opacity condition post-treatment.

These machine learning models may be configured, as discussed in further detail below, to use at least measurements of physical parameters of a current patient's opacity condition, as input, and generate, as output, one or more vitreous opacity severity measurements (hereinafter "opacity severity measurements"), including a severity score of the current patient's opacity condition. Herein, severity refers to the extent or degree of visual impairment (e.g., negative impact on the patient's visual function) as caused by the opacity condition. More severe instances of vitreous opacities cause greater visual impairment as compared to less severe instances thereof, and may require more intensive forms of treatment to correct. In certain embodiments, the severity score is a scaled score corresponding with a value on a scale of 1-100, 1 being least severe (i.e., lowest severity) and 100 being most severe (i.e., highest severity).

As a result, the surgeon can be provided with an objective and more accurate determination of severity of the current patient's opacity condition. Using this information, the surgeon is able to determine an optimal form of treatment for the current patient. Note that, as described in further detail below, the input to these machine learning models may include additional information, such as data points associated with the current patient's demographic information, pre-treatment self-reported severity data, as well as other information about the current patient's opacity condition, etc.

Various techniques may be used to train and deploy machine learning models that generate an opacity severity measurement for a current patient. Various deployments are illustrated in FIGS. 1A-1C. For example, FIG. 1A illustrates a deployment in which machine learning models are trained on a remote server and are deployed to a user console used by a surgeon during patient examination. FIG. 1B illustrates a deployment in which the machine learning models are trained and deployed on a remote server accessible through the user console. Finally, FIG. 1C illustrates a deployment in which the machine learning models are trained on a remote server and are deployed to a computing system integral with a diagnostic device, e.g., an imaging device. It should be recognized, however, that various other techniques for training and deploying machine learning models that generate opacity severity measurements for a current patient may be contemplated, and that the deployments illustrated in FIGS. 1A-1C are non-limiting, illustrative examples.

FIG. 1A illustrates an example computing environment 100A in which diagnostic devices 110, server 120, and user console 130 are connected via a network in order to train one or more machine learning models for use in generating opacity severity measurements for a current patient based, at least in part, on measurements of physical parameters of the current patient's opacity condition, as provided by the diagnostic devices 110. For readability, the one or more machine learning models are referred to herein as an "ML model," which covers both a single ML model and multiple ML models.

Diagnostic devices 110 are generally representative of any suitable devices that can generate, or facilitate generation of, information about the vitreous, such as measurements of physical parameters of vitreous opacities afflicting a current patient. Herein, physical parameters of the vitreous opacities refer to individual (e.g., of a singular opacity or of individual opacities of a plurality) or collective (e.g., of a collective plurality) parameters such as the number, size, shape (e.g., Weiss Ring, cobweb, or cloud), surface area, density or relative transparency, movement, location (e.g., along the visual axis or in the periphery thereof), distance to the retina and/or the crystalline lens, etc. The measurements may include, in some embodiments, e.g., measurement values of the corresponding physical parameters. In certain embodiments, the measurements include data points associated with one or more measurements of physical parameters of vitreous opacities afflicting a current patient.

In certain embodiments, diagnostic devices 110 may generate raw data from which measurements may be derived. In such a case, the raw data may include, for example, two-dimensional cross-sectional images of the eye; two-dimensional wide-angle images of the eye; three-dimensional images of the eye; two-dimensional topographic maps of the eye; or other data from which measurements of physical parameters may be derived. Generally, any number of diagnostic devices $110_1$-$110_n$ may be included in computing environment 100A and may be used to generate different types of data that may be used as input into an ML model that generates opacity severity measurements. Each diagnostic device 110 in the computing environment 100A may generate measurements, or associated data points, of one or more physical parameters of a patient's opacity condition, and more generally, the patient's eye, and provide the measurements, or associated data points, to user console 130, server 120, and/or repository 140.

In one example, one of diagnostic devices 110 may include an optical coherence tomography (OCT) device, such as a time or frequency domain OCT device, a Fourier OCT device, etc. For example, a diagnostic device 110 may include an OCT device that can generate one-dimensional (e.g., from a central point), two-dimensional, and/or three-dimensional data (e.g., imaging data) for the current patient's eye from which measurements of various individual or collective physical parameters of the current patient's opacity condition may be derived. From the data, the OCT device can derive various relevant measurements for characterizing the severity of the current patient's opacity condition, including number, size, shape (e.g., Weiss ring, cobweb, or cloud), surface area, density or relative transparency, movement, location (e.g., along the visual axis or in the periphery thereof), distance to the retina and/or the crystalline lens, etc.

Another one of diagnostic devices 110 may include a scanning laser ophthalmoscopy (SLO) device that can generate high quality and wide-angle two-dimensional images of the current patient's fundus in real-time. Similar to OCT, the SLO device can derive various relevant measurements for characterizing the severity of the current patient's opacity condition, including the number, size, shape, surface area, density or relative transparency, movement, location, and distance to the retina and/or the crystalline lens thereof. In such embodiments, the presence of vitreous opacities in the current patient's eye may be indicated by the presence of unfocused structures in the broad, two-dimensional SLO image.

Yet other examples of the diagnostic devices 110 may include a dark field microscope, an ultrasound device, and a multispectral imaging system, such as an 8-band or 10-band multispectral retinal imaging system. Generally, any suitable diagnostic devices 110 may be utilized, alone or in combination, to derive measurements of the various physical parameters of the current patient's opacity condition.

Server 120 is generally representative of a single computing device or cluster of computing devices on which training data sets can be generated and used to train an ML model for generating opacity severity measurements. Server 120 is communicatively coupled to historical patient data repository 140 (hereinafter "repository 140"), which stores records of historical patients. In certain embodiments, repository 140 may be or include a database server for receiving information from server 120, user console 130, and/or diagnostic devices 110 and for storing the information in corresponding patient records in a structured and organized manner.

In certain aspects, each patient record in repository 140 includes information such as the patient's demographic information, recorded measurements of physical parameters of the patient's opacity condition pre-treatment, pre-treatment self-reported severity data, the patient's opacity severity measurements, information about the treatment, if any, such as the type of treatment, and/or post-treatment self-reported severity data, as well as other post-treatment information, such as measurements of physical parameters of the patient's opacity condition post-treatment. For example, the demographic information for each patient may include patient age, gender, ethnicity, and the like. The measurements of physical parameters of the patient's opacity condition may include raw data or measurements generated by or provided by an OCT device, an SLO device, a dark field microscope, a multispectral imaging system, etc., as discussed above. Each patient record may also include pre-treatment self-reported severity data, which includes one or more data points indicative of the patient's own assessment of their visual impairment resulting from their opacity condition. For example, in certain embodiments, the self-reported severity data includes a subjective severity score on a three tier scale of "mild," "moderate," or "severe," or on a scale of 1-100, as described above. In certain cases, the self-reported severity data is based on responses provided by the patient in a Visual Function Questionnaire (VFQ), which may evaluate the patient's assessment of their vision-specific quality of life (QOL). Similar to pre-treatment self-reported severity data, post-treatment self-reported severity data includes one or more data points indicative of the patient's own assessment of their visual impairment after treatment. For example, in certain embodiments, the post-treatment severity data may be a subjective severity score (e.g., mild, moderate, severe), and/or may be based on VFQ responses provided by the patient after treatment of their opacity condition. Other post-treatment information in repository 140 may include measurements of physical parameters of the patient's opacity condition after treatment thereof.

Server 120 uses these records of historical patients to generate data sets for use in training an ML model that can provide opacity severity measurements to a surgeon for informing proper treatment strategy for a current patient. More specifically, as illustrated in FIG. 1A, server 120 includes a training data generator 122 (hereinafter "TDG 122") and model trainer 124. TDG 122 retrieves data from repository 140 to generate data sets for use by model trainer 124 to train ML model 125.

Model trainer 124 includes or refers to one or more machine learning algorithms (referred to hereinafter as "ML algorithms") that are configured to use training data sets to train ML model 125. In certain embodiments, a trained ML model refers to a function, e.g., with weights and parameters, that is used to generate opacity severity measurements for a given set of inputs. Various ML algorithms may be used to generate different types of outputs for a given set of inputs.

The ML algorithms may generally include a supervised learning algorithm, an unsupervised learning algorithm, and/or a semi-supervised learning algorithm. Unsupervised learning is a type of machine learning algorithm used to draw inferences from data sets consisting of input data without labeled responses. Supervised learning is the machine learning task of learning a function that, for example, maps an input to an output based on example input-output pairs. Supervised learning algorithms, generally, include regression algorithms, classification algorithms, decision trees, neural networks, etc. A description of a labeled data set is provided below.

Once trained and deployed, based on a certain set of inputs associated with a current patient, including the measurements of physical parameters of the patient's opacity condition, demographic information, and pre-treatment self-reported severity data, ML model 125 is able to generate or predict opacity severity measurements for the current patient, as output. In certain aspects, model trainer 124 trains ML a model 125 configured to take a set of inputs associated with a current patient and provide opacity severity measurements, including an objective vitreous opacity severity score, to the surgeon. The surgeon may then utilize the severity measurements to select an appropriate treatment strategy for the current patient. To train ML model 125, model trainer 124 may utilize a labeled data set provided by TDG 122 that includes a plurality of featurized data samples including a plurality of features associated with demographic information, measurements of physical parameters of the opacity condition generated by a number of diagnostic devices (e.g., an OCT device, an SLO device, a dark field microscope, and/or a multispectral imaging system), pre-treatment and post-treatment self-reported severity data, an improvement score (e.g., difference between pre-treatment and post-treatment self-reported severity data), etc.

A variety of ML models may be trained based on this labeled data set. In one example, the ML model 125 may be trained to predict an objective pre-treatment severity assessment. In such an example, to train such a model, the model trainer 124 may run certain or all features from each sample in the data set associated with historical patients through the ML model 125. The features may include: the historical patient's demographic information (e.g., age, gender, ethnicity, race, etc.); pre-treatment information associated with the patient's opacity condition (e.g., number, size, shape, surface area, density or relative transparency, movement, location, distance to the retina and/or the crystalline lens, for individual or collective vitreous opacities of a historical patient as generated by a number of diagnostic devices, etc.); pre-treatment self-reported severity data provided by the historical patient in a Visual Function Questionnaire or a similar test, etc. Running each sample through the ML model 125 results in a prediction of an objective severity score that is then compared with the patient's self-reported severity score. After running a large number of samples through ML model 125 and continuing to adjust the weights based thereon, at a certain point in time, the ML model 125 starts predicting objective severity scores that are more in-line with subjective severity scores provided by non-outlier patients in the data set.

In another example, a different ML model 125 may be trained by the model trainer 124 by first selecting samples in the data set associated with patients who were treated and who saw an improvement in their visual impairment after the treatment, as indicated by their improvement score based on a comparison between each patient's pre-treatment and post-treatment self-reported severity assessment. Note that patients who were treated and who saw an improvement in their visual impairment after the treatment are likely patients whose pre-treatment self-reported assessment of their visual impairment have a higher correlation with their opacity condition. On the other hand, patients who were treated and who saw no improvement or a deterioration in their visual impairment are likely patients whose pre-treatment self-reported assessment of their visual impairment have a lower correlation with their opacity condition. Therefore, to train an ML model 125 that is able to predict a more objective severity assessment, samples associated with patients who saw an improvement (e.g., indicated by an improvement score of above a certain threshold) in their visual impairment after the treatment are selected.

Having selected the right samples, the model trainer 124 may then run certain features from each sample through the ML model 125, where the features may include: the historical patient's demographic information; information associated with the patient's opacity condition; and pre-treatment self-reported severity data provided by the historical patient in a Visual Function Questionnaire or a similar test.

Running each sample through the ML model 125 results in a prediction of an objective severity assessment, which is then compared with the actual pre-treatment self-reported severity score provided by the historical patient. Any difference between the two would be considered an error, which model trainer 124 may work to reduce by adjusting the weights associated with the different features or variables in the ML model 125. By running a large number of samples through ML model 125 and continuing to adjust the weights based thereon after a certain point, the ML model 125 starts making accurate determinations of an objective severity score.

In another example, the ML model 125 may be trained to predict an improvement score indicative of the likelihood of improving a current patient's visual impairment by performing a certain treatment. For such a model, the model trainer 124 may first select samples in the data set associated with historical patients who were treated with the selected treatment, and then run certain features from each sample through the ML model 125, where the features may include: the historical patient's demographic information; information associated with the patient's opacity condition; pre-treatment self-reported severity data provided by the historical patient in a Visual Function Questionnaire or a similar test; an improvement score, etc. Running each sample through the ML model 125 results in a prediction of an improvement, which is then compared with the actual improvement score of the historical patient. Any difference between the two would be considered an error, which model trainer 124 may work to reduce by adjusting the weights associated with the different features or variables in the ML model 125.

A variety of other ML models may also be trained and utilized. Once an ML model 125 is trained, it is ready to be deployed for taking a set of inputs about a current patient and generating opacity severity measurements (e.g., an objective severity assessment, an improvement score prediction, etc., that can be utilized to inform treatment strategy for the current patient). In the example of FIG. 1A, the trained ML model 125 may then be deployed for use at user console 130 for generating opacity severity measurements for a current patient, as described in further detail below.

In some aspects, ML model 125 may be a deep learning model that is trained to generate opacity severity measurements. Deep learning models may include, for example, convolutional neural networks (CNNs), adversarial learning algorithms, generative networks, or other deep learning algorithms that can learn relationships in datasets that may not be explicitly defined in the data used to train such models. In such a case, ML model 125 may be trained using raw data captured by diagnostic devices 110, such as two-dimensional or three-dimensional images from which typical numerical measurements of physical parameters of vitreous opacities can be derived. ML model 125 may, for example, map an input to different neurons in one or more layers of a deep learning model (e.g., where the ML model is generated using neural networks), where each neuron in the ML model 125 represents new features in an internal representation of an input that are learned over time. These neurons may then be mapped to an output representing opacity severity measurements, as discussed above.

After ML model 125 is trained, model trainer 124 deploys the ML model 125 to user console 130 for use in generating opacity severity measurements for a current patient. The diagnostic devices 110 generate measurements of the physical parameters of the current patient's opacity condition, and transmit these measurements to server 120, user console 130, and/or repository 140. Note that in embodiments where diagnostic devices 110 transmit the data points to server 120 or user console 130 (as opposed to directly transmitting them to repository 140), the data points may at some later point be committed by server 120 or user console 130 to repository 140, which stores the measurements in the current patient's record.

User console 130 then retrieves the data points (from the repository 140 and/or from temporary memory at the user console 130) and inputs the data points and other patient information (e.g., the current patient's demographic information, self-reported severity data, etc.) into the ML model 125. User console 130 then outputs the severity measurements generated by the ML model 125. The record in the repository 140, including the measurements for one or more physical parameters of the current patient's opacity condition, which is mapped to the severity measurements generated by the ML model 125, is then converted into a new sample in a training dataset that is used to retrain the ML model 125. More generally, each time a new (i.e., current) patient is examined, information about the new patient may be saved in repository 140 to supplement the training dataset(s), and the supplemented training dataset(s) may be used to retrain the ML model 125.

Once the trained ML model 125 is deployed, as further described below, TDG 122 continues to augment the training data sets with information relating to patients for whom the deployed ML model 125 provided opacity severity measurements. For example, in the embodiments of FIG. 1A, a surgeon may use user console 130 to generate, using the deployed ML model 125, opacity severity measurements (e.g., including vitreous opacity predicted objective severity assessment, a predicted improvement score, etc.), for a new patient. In that example, as described above, a new record is then added to repository 140 that may include information about the new patient, including demographic information, measurements of physical parameters of the patient's opacity condition, self-reported severity data, and/or other information related to the patient's opacity condition, such as post-treatment information. TDG 122 then augments the data set(s) for retraining the ML model 125. In certain aspects, TDG 122 augments the data set(s) every time information about a new (i.e., current) patient becomes available. In certain other aspects, TDG 122 augments the data set(s) with a batch of new patient records, which may be more resource efficient. For example, once the number of new patient records hits 100 (or, more generally, some threshold number), TDG 122 may augment the data set(s) using information associated with the 100 new patient records. In such an example, 100 new samples are then made available to model trainer 124 to retrain ML model 125 with.

User console 130 is generally representative of a computing device or system that is communicatively coupled to server 120, repository 140, and/or diagnostic devices 110. In certain embodiments, user console 130 may be a desktop computer, laptop computer, tablet computer, smartphone, or other computing device(s). For example, user console 130 may be a computing system used at the surgeon's office or clinic. In another example, user console 130 may be a device console used by a surgeon in an examination room to perform an examination of a current patient. For example, the user console may be a console for one or more of the diagnostic devices 110. In yet another example, user console 130 may be a surgical console that is capable of performing laser vitreolysis and small-gauge vitrectomy.

In the example of FIG. 1A, the trained ML model 125 is deployed by server 120 to user console 130 for generating, for a current patient, opacity severity measurements that could be utilized by, e.g., the surgeon, to inform determination of a treatment strategy for the current patient. As illustrated, user console 130 includes a patient data recorder ("PDR") 132 and a severity measurement generator ("SMG") 134. SMG 134 generally refers to a software module or a set of software instructions or algorithms, including ML model 125, which take a set of inputs about a current patient and generate, as output, opacity severity measurements. In certain embodiments, SMG 134 is configured to receive the set of inputs from at least one of repository 140, diagnostic devices 110, a user interface or some other component of user console 130, and other computing devices that a medical practitioner/office may use to record information about the current patient. In certain embodiments, SMG 134 outputs the opacity severity measurements to a display device communicatively coupled with user console 130, prints the severity measurements, generates and transmits one or more electronic messages, including severity measurements, to a destination device (e.g., a connected device, such as a tablet, smartphone, wearable device, etc.), or the like.

User console 130 also comprises a PDR 132, which receives or generates data regarding the opacity condition of the current patient, as well as other patient data for the current patient. As described above, patient data may include self-reported severity data for the current patient, demographic data, as well as any additional relevant information, such as post-treatment information. In the embodiments of FIG. 1A, PDR 132 transmits the current patient data to repository 140 and/or server 120, where the current patient data may be converted by TDG 122 into a new sample in a training data set that is used to retrain the ML model 125.

FIG. 1B illustrates another example computing environment 100B in which training and use of the machine learning models to generate opacity severity measurements are performed. As illustrated, computing environment 100B includes one or more diagnostic devices 110, server 120, user console 130, and historical patient data repository 140. In the example of FIG. 1B, TDG 122, model trainer 124, PDR 132, and SMG 134 all execute on server 120. All of these software modules function identically or at least substantially similar to what was described in relation to FIG. 1A. In the example of FIG. 1B, diagnostic devices 110 may transmit the measurements of physical parameters of vitreous opacities for a current patient to server 120 and/or repository 140. SMG 134 generates the opacity severity measurements, based on a set of inputs associated with a current patient, and transmits the opacity severity measurements to user console 130. User console 130 then transmits back patient data to PDR 132, which processes and store the corresponding information at repository 140.

FIG. 1C illustrates an example computing environment 100C in which generating opacity severity measurements are performed on a diagnostic device 110. As illustrated, computing environment 100C includes a diagnostic device 110, a server 120, and a historical patient data repository 140. In the example of FIG. 1C, PDR 132 and SMG 134 all execute on a diagnostic device 110. All of these software modules function identically or at least substantially similar to what was described in relation to FIGS. 1A and 1B.

As illustrated, diagnostic device 110 includes diagnostic hardware/software 112, which generally refers to the hardware and software components and modules associated with either an OCT device, an SLO device, a multispectral imaging system, etc. Diagnostic device 110 may also include a user interface and/or a display device, enabling a user to input and/or view information as it relates to the functionality of PDR 132 and SMG 134.

Example Methods for Generating Opacity Severity Measurements Using Machine Learning Models FIG. 2 illustrates example operations 200 that may be performed by a computing system to train and use ML models to generate opacity severity measurements, including an objective vitreous opacity severity score, for a current patient's opacity condition, based at least on measurements of physical parameters of the current patient's opacity condition, in accordance with certain aspects described herein. Operations 200 may be performed by one or more of a user console 130, server 120, or diagnostic device 110 illustrated in FIGS. 1A-1C.

As illustrated, operations 200 may begin at block 210, where the system retrieves a set of historical patient records. Each record in the set of historical patient records includes information about a specific historical patient. As discussed, for example, each record includes demographic information, measurements of physical parameters of the patient's opacity condition pre-treatment, pre-treatment self-reported severity data, other information related to the patient's opacity condition such as treatment and post-treatment information, as well as any opacity severity measurements, as recorded for the historical patient. In certain embodiments, other information related to the patient's opacity condition includes type of treatment and/or post-treatment self-reported severity data, as well as other post-treatment information such as measurements of physical parameters of the patient's opacity condition post-treatment.

At block 220, the system generates a training data set by mapping, for each historical patient of a number of historical patients, the patient's demographic information, recorded measurements of physical parameters of the patient's opacity condition pre-treatment, pre-treatment self-reported severity data, information about the treatment, if any, as well as post-treatment data to the patient's opacity severity measurements. Generally, by mapping these historical patients' data points and parameters to their opacity severity measurements, the training data set may allow for ML models to be trained to generate opacity severity measurements given at least an input of measurements of physical parameters of vitreous opacities for a future (i.e., current) patient.

At block 230, the system trains one or more ML models based on the training data set. The trained ML models may be trained to generate one or more severity measurements, including an objective vitreous opacity severity score, for the current patient's opacity condition. The ML models may be MIMO models or may be a set of MISO models.

At block 240, the system deploys the trained ML models for use. The trained ML models may be deployed to one or more server computers, a user console, a diagnostic device in which a computing device is integrated, or the like, as illustrated for example in FIGS. 1A-1C, or even a computing device not shown in FIGS. 1A-1C.

Figure 3:
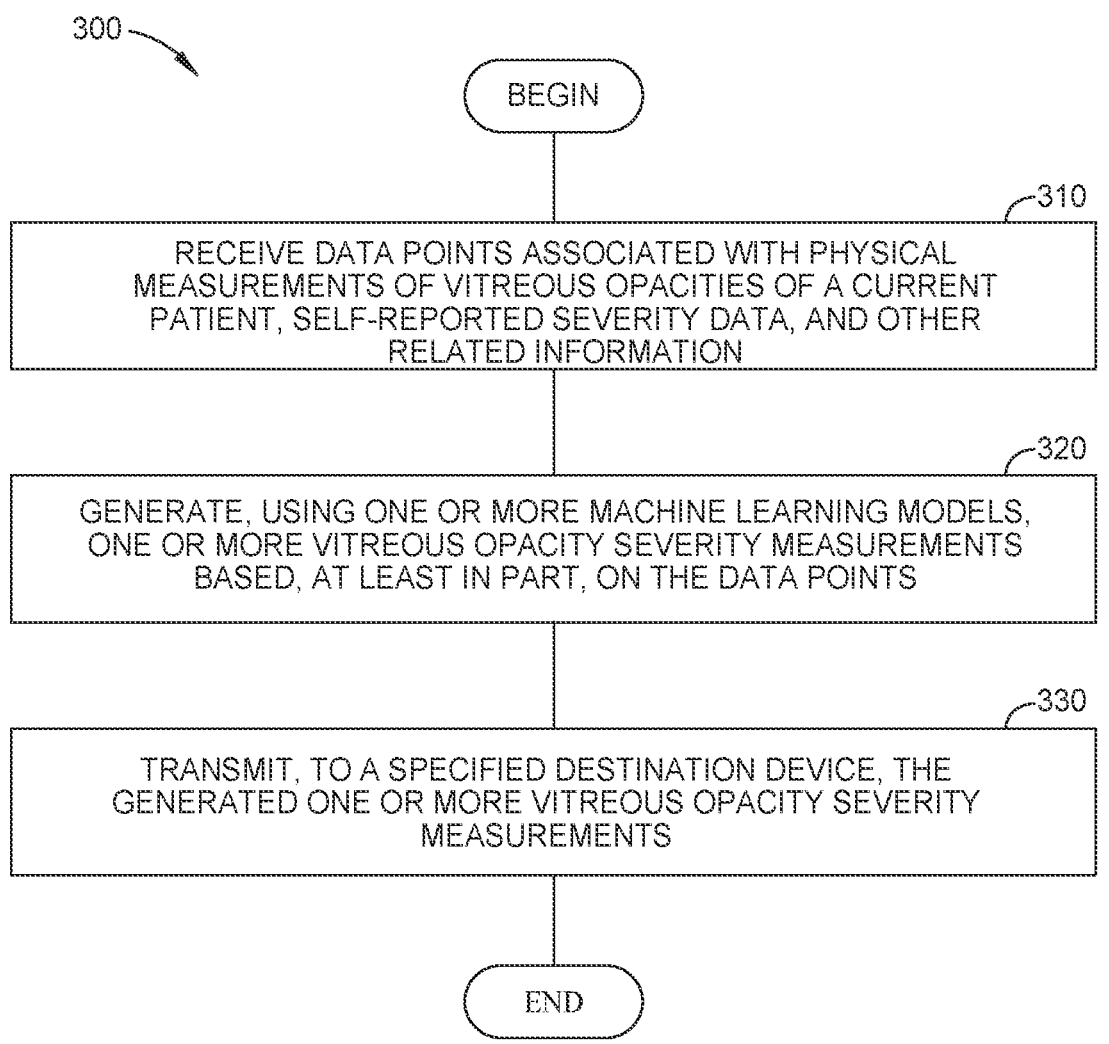
FIG. 3 illustrates example operations that may be performed by one or more computing systems to determine a severity of a patient's vitreous opacity condition, in accordance with certain aspects described herein.

FIG. 3 illustrates example operations 300 that may be performed by one or more computing systems to generate opacity severity measurements, including an objective vitreous opacity severity score, for a current patient's opacity condition, based at least on measurements of physical parameters of the current patient's opacity condition, in accordance with certain aspects described herein. Operations 300 may be performed, for example, by a severity measurements generator, such as SMG 134 illustrated in FIGS. 1A-1C.

At block 310, the system receives information associated with the patient, such as demographic information, measurements of physical parameters of a current patient's opacity condition, pre-treatment self-reported severity data, and other information related to the current patient's opacity condition.

At block 320, the system generates, using trained ML models, one or more opacity severity measurements, including an objective severity score. The generated opacity severity measurements may be based, at least in part, on the data points above. The opacity severity measurements, along with all of the other relevant data points associated with the current patient, may then be added to the training data set described above for retraining the ML models.

At block 330, the system transmits, to a specified destination device, the generated opacity severity measurements. The specified destination device may be a user console through which planning for ophthalmic treatment is performed (which may be communicatively coupled with one or more diagnostic devices via a network or a point-to-point connection or integral with a diagnostic device) or a device capable of receiving electronic messaging from another device.

Figure 4:
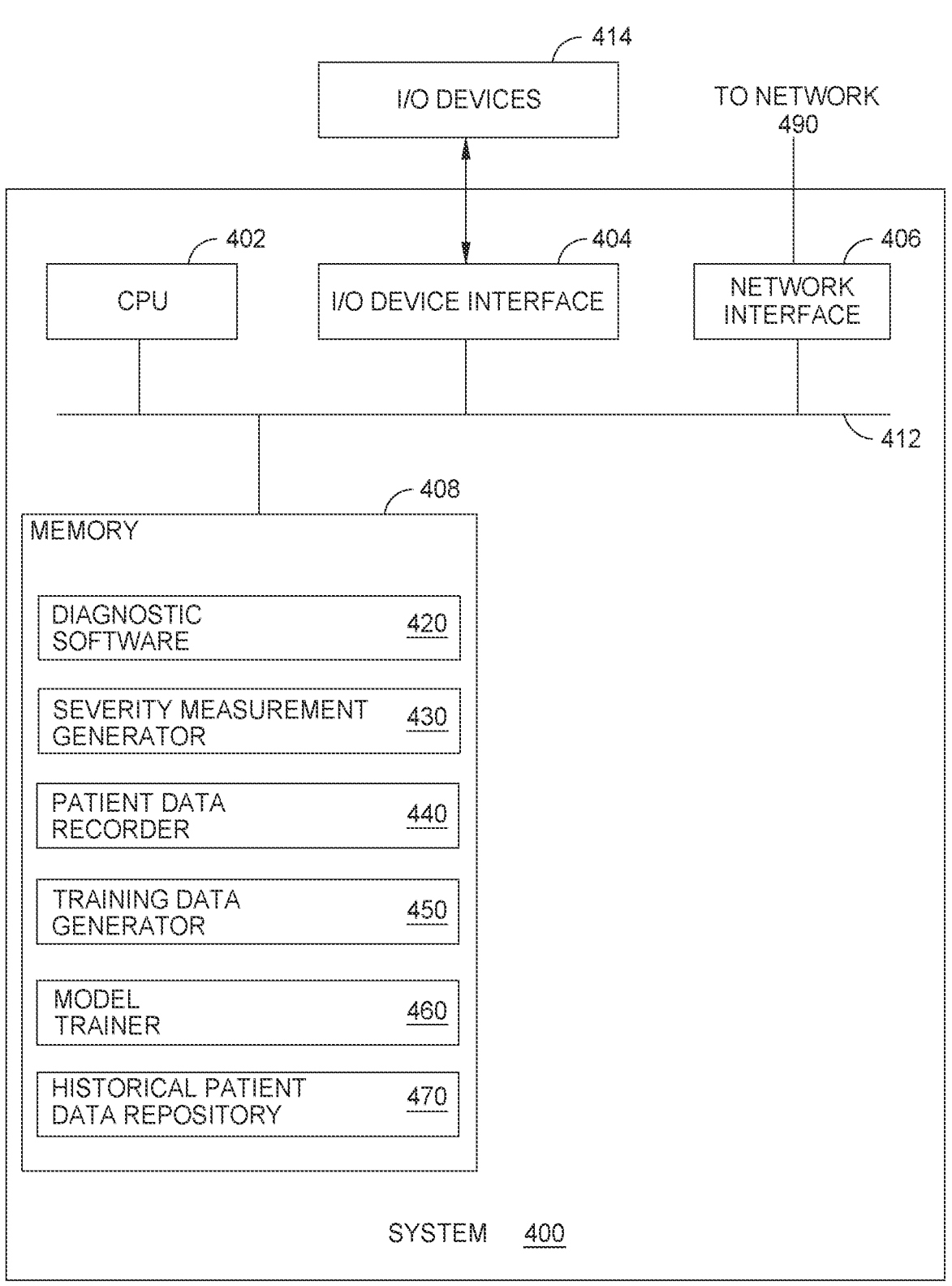
FIG. 4 illustrates an example system on which embodiments of the present disclosure can be performed.

Example System for Generating Opacity Severity
Measurements Using Machine Learning Models FIG. 4 illustrates an example system 400 that uses machine learning models to aid in performing ophthalmic examinations and procedures. For example, system 400 may comprise one or more of the diagnostic devices 110, server 120, and/or user console 130 illustrated in FIG. 1.

As shown, system 400 includes a central processing unit (CPU) 402, one or more I/O device interfaces 404 that may allow for the connection of various I/O devices 414 (e.g., keyboards, displays, mouse devices, pen input, etc.) to the system 400, network interface 406 through which system 400 is connected to network 490 (which may be a local network, an intranet, the internet, or any other group of computing devices communicatively connected to each other), a memory 408, storage 410, and an interconnect 412.

CPU 402 may retrieve and execute programming instructions stored in the memory 408. Similarly, the CPU 402 may retrieve and store application data residing in the memory 408. The interconnect 412 transmits programming instructions and application data, among the CPU 402, I/O device interface 404, network interface 406, memory 408, and storage 410.

CPU 402 is included to be representative of a single CPU, multiple CPUs, a single CPU having multiple processing cores, and the like.

Memory 408 is representative of a volatile memory, such as a random access memory, and/or a nonvolatile memory, such as nonvolatile random access memory, phase change random access memory, or the like. As shown, memory 408 includes diagnostic software or instructions 420, SMG 430, PDR 440, TDG 450, model trainer 460, and repository 470. Diagnostic software 420 is generally configured to receive raw image or reflectivity data from optical hardware that is a part of system 400 (e.g., OCT or SLO scanner, etc.) or a connected measurement device (e.g., OCT device, SLO device, dark field microscope, multispectral imaging device, etc.) and generate data points associated with measurements of one or more physical parameters of vitreous opacities therefrom. Diagnostic software 420 may output the data points associated with measurements of physical parameters to SMG 430 for use in providing severity measurements, including providing an objective severity score for a patient's opacity condition.

SMG 430 comprises or uses one or more trained and deployed ML models trained by model trainer 460. SMG 430 generally processes at least one or more data point associated with a measurement of a physical parameter received from diagnostic software 420 or from an external source, as well as patient demographic data, self-reported patient parameters, and other related information, and generates, using the one or more ML models, one or more severity measurements.

PDR 440 generally allows for a user of system 400 to record patient data, as previously defined. PDR 440 may output the data to repository 470 for storage and future use in generating training data sets used to train the one or more ML models deployed to and used by SMG 430.

As discussed, TDG 450 generally uses historical patient information (e.g., stored in historical patient data repository 470) to generate training data sets that may be used by model trainer 460 to train the one or more ML models deployed to and used by SMG 430.

Model trainer 460 generally trains the one or more ML models used by SMG 430 in generating opacity severity measurements for a current patient. As discussed, model trainer 460 may use the training data sets generated by training data generator 450 to train the ML models and may deploy the trained ML models to SMG 430 (or a remote system) for use.

As described above, embodiments of the present disclosure provide systems and methods utilizing one or more machine learning models in determining a severity of vitreous opacities afflicting a current patient. By using the systems and methods herein, a physician, e.g., ophthalmic surgeon, is able to leverage a large universe of historical patient data in order to determine a more accurate severity of vitreous opacities afflicting the current patient, which may, in turn, be utilized to determine an optimized treatment strategy for the current patient. Accordingly, the techniques herein improve the medical field by increasing the accuracy of vitreous disease diagnostics, thereby leading to better-informed selection of treatment strategies.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A system for generating vitreous opacity severity measurements, comprising:
   one or more ophthalmic diagnostic devices configured to generate one or more measurements of a vitreous opacity condition of a current patient, the one or more ophthalmic diagnostic devices including one or more of an optical coherence tomography (OCT) device, a scanning laser ophthalmoscopy (SLO) device, a dark field microscope, or a multi-spectral imaging device;
   a memory comprising executable instructions;
   a processor communicatively coupled with the one or more ophthalmic diagnostic devices and in data communication with the memory and configured to execute the instructions to generate, using one or more trained machine learning models, a severity assessment of the vitreous opacity condition based on the one or more measurements of the vitreous opacity condition of the current patient, wherein:
   the one or more trained machine learning models are trained based on at least one historical data set, wherein each entry in the at least one historical data set includes one or more measurements of a vitreous opacity condition for a historical patient, the measurements indicating one or more of a number, a size, a shape, a surface area, a relative transparency, a movement, a location, and a distance to a retina and/or a crystalline lens of one or more vitreous opacities of the historical patient; and
   the memory is further configured to execute the instructions to:
   map the one or more measurements of the vitreous opacity condition of the current patient to the severity assessment; and
   convert the one or more measurements of the vitreous opacity condition of the current patient and the severity assessment into a sample for retraining the one or more trained machine learning models.

2. The system of claim 1, wherein the severity assessment includes a severity score on a scale of 1-100, wherein a severity score of 1 corresponds to a lowest severity and a severity score of 100 corresponds to a highest severity.

3. The system of claim 1, wherein the measurements of the vitreous opacity condition of the current patient are derived from one or more of a two-dimensional cross-sectional image of the current patient's eye, a two-dimensional wide-angle image of the current patient's eye, a three-dimensional image of the current patient's eye, and a two-dimensional topographic map of the current patient's eye.

4. The system of claim 1, wherein the ophthalmic diagnostic devices further include an ultrasound device.

5. The system of claim 1, wherein generating the severity assessment is further based on demographic information of the current patient.

6. The system of claim 5, wherein each entry in the at least one historical data set further includes demographic information of the historical patient.

7. The system of claim 1, wherein generating the severity assessment is further based on self-reported data indicative of the current patient's own assessment of their vitreous opacity condition.

8. The system of claim 7, wherein the self-reported data indicative of the current patient's own assessment of their vitreous opacity condition is based on responses provided by the current patient in a Visual Function Questionnaire (VFQ).

9. The system of claim 1, wherein each entry in the at least one historical data set further includes self-reported data indicative of the historical patient's own assessment of their vitreous opacity condition.

10. The system of claim 9, wherein the self-reported data indicative of the historical patient's own assessment of their vitreous opacity condition is based on responses provided by the historical patient in a Visual Function Questionnaire (VFQ).

11. The system of claim 1, wherein each entry in the at least one historical data set further includes post-treatment information for the historical patient.

12. The system of claim 11, wherein the post-treatment information includes one or more measurements of the vitreous opacity condition of the historical patient after treatment.

13. The system of claim 11, wherein the post-treatment information includes self-reported data indicative of the historical patient's own assessment of their vitreous opacity condition after treatment.

14. The system of claim 11, wherein the post-treatment information includes an improvement score indicative of the improvement in the historical patient's vitreous opacity condition after treatment.

15. The system of claim 14, wherein the severity assessment includes an improvement score indicative of a predicted improvement in the current patient's vitreous opacity condition after treatment.

16. A method of determining a severity of a vitreous opacity condition, comprising:

generating, using one or more ophthalmic diagnostic devices, one or more measurements of a vitreous opacity condition of a current patient, the one or more ophthalmic diagnostic devices including one or more of an optical coherence tomography (OCT) device, a scanning laser ophthalmoscopy (SLO) device, a dark field microscope, or a multi-spectral imaging device; and generating, using one or more trained machine learning models, a severity assessment of the vitreous opacity condition based on the one or more measurements of the vitreous opacity condition of the current patient, wherein:

the one or more trained machine learning models are trained based on at least one historical data set, wherein each entry in the at least one historical data set includes one or more measurements of a vitreous opacity condition for a historical patient, the measurements corresponding with one or more of a number, a size, a shape, a surface area, a relative transparency, a movement, a location, and a distance to a retina and/or a crystalline lens of one or more vitreous opacities of the historical patient;

mapping the one or more measurements of the vitreous opacity condition of the current patient to the severity assessment; and converting the one or more measurements of the vitreous opacity condition of the current patient and the severity assessment into a sample for retraining the one or more trained machine learning models.

17. The method of claim 16, wherein the severity assessment includes a severity score on a scale of 1-100, wherein a severity score of 1 corresponds to a lowest severity and a severity score of 100 corresponds to a highest severity.

18. The method of claim 16, wherein the measurements of the vitreous opacity condition of the current patient are derived from one or more of a two-dimensional cross-sectional image of the current patient's eye, a two-dimensional wide-angle image of the current patient's eye, a three-dimensional image of the current patient's eye, and a two-dimensional topographic map of the current patient's eye.

19. The method of claim 16, wherein the ophthalmic diagnostic devices further include an ultrasound device.

20. The method of claim 16, wherein generating the severity assessment is further based on demographic information of the current patient.

21. The method of claim 20, wherein each entry in the at least one historical data set further includes demographic information of the historical patient.

22. The method of claim 16, wherein generating the severity assessment is further based on self-reported data indicative of the current patient's own assessment of their vitreous opacity condition.

23. The method of claim 22, wherein the self-reported data indicative of the current patient's own assessment of their vitreous opacity condition is based on responses provided by the current patient in a Visual Function Questionnaire (VFQ).

24. The method of claim 16, wherein each entry in the at least one historical data set further includes self-reported data indicative of the historical patient's own assessment of their vitreous opacity condition.

25. The method of claim 24, wherein the self-reported data indicative of the historical patient's own assessment of their vitreous opacity condition is based on responses provided by the historical patient in a Visual Function Questionnaire (VFQ).

26. The method of claim 16, wherein each entry in the at least one historical data set further includes post-treatment information for the historical patient.

27. The method of claim 26, wherein the post-treatment information includes one or more measurements of the vitreous opacity condition of the historical patient after treatment.

28. The method of claim 26, wherein the post-treatment information includes self-reported data indicative of the historical patient's own assessment of their vitreous opacity condition after treatment.

29. The method of claim 26, wherein the post-treatment information includes an improvement score indicative of the improvement in the historical patient's vitreous opacity condition after treatment.

30. The method of claim 29, wherein the severity assessment includes an improvement score indicative of a predicted improvement in the current patient's vitreous opacity condition after treatment.

* * * * *